(12) United States Patent
Farazi

(10) Patent No.: US 8,005,533 B1
(45) Date of Patent: Aug. 23, 2011

(54) IMPLANTABLE SYSTEMS AND METHODS FOR MONITORING MYOCARDIAL ELECTRICAL STABILITY BY DETECTING PVC INDUCED T-WAVE ALTERNANS REVERSALS

(75) Inventor: Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 978 days.

(21) Appl. No.: 11/669,744

(22) Filed: Jan. 31, 2007

(51) Int. Cl.
*A61B 5/0452* (2006.01)
(52) U.S. Cl. ...................................... 600/515
(58) Field of Classification Search .............. 600/509, 600/515, 516; 607/9
See application file for complete search history.

(56) References Cited

U.S. PATENT DOCUMENTS

| 6,915,156 | B2 | 7/2005 | Christini et al. | |
|---|---|---|---|---|
| 2005/0004608 | A1* | 1/2005 | Bullinga | 607/9 |
| 2006/0116592 | A1* | 6/2006 | Zhou et al. | 600/509 |
| 2006/0116596 | A1* | 6/2006 | Zhou et al. | 600/516 |

FOREIGN PATENT DOCUMENTS

| WO | 2005006956 A2 | 1/2005 |
|---|---|---|

OTHER PUBLICATIONS

Narayan et al., "T-wave Alternans Phase Following Ventricular Extrasystoles Predicts Arrhythmia-Free Survival," Heart Rhythm, vol. 2, No. 3, Mar. 2005: 234-241.*
Rubenstein et al., "Premature Beats Elicit a Phase Reversal of Mechanoelectrical Alternans in Cat Ventricular Myocytes: A Possible Mechanism for Reentrant Arrhythmias," Circulation. 1995;91:2001-214.
Brugada et al., "Significance of Ventricular Arrhythmias Initiated by Programmed Ventricular Stimulation: The Importance of the Type of Ventricular Arrhythmia Induced and the Number of Premature Stimuli Required," Circulation. 1984;69:87-92.
Christini et al., "Endocardial Detection of Repolarization Alternans," IEEE Transaction on Biomedical Engineering, vol. 50, No. 7, Jul. 2003: 855-862.

* cited by examiner

*Primary Examiner* — Eric D. Bertram
(74) *Attorney, Agent, or Firm* — Theresa Takeuchi; Steven M. Mitchell

(57) ABSTRACT

Embodiments of the present invention relate to implantable systems, and methods for use therewith, for assessing a patients' myocardial electrical stability. Implanted electrodes are used to obtain an electrogram (EGM) signal, which is used to identify periods when the patient experiences T-wave alternans. Additionally, the EGM signal is used to determine whether premature ventricular contractions (PVCs) cause phase reversals of the T-wave alternans. The patient's myocardial electrical stability is assessed based on whether, and in a specific embodiment the extent to which, PVCs cause phase reversals of the T-wave alternans. This abstract is not intended to be a complete description of, or limit the scope of, the invention.

20 Claims, 6 Drawing Sheets

IMPLANTABLE SYSTEMS AND METHODS FOR MONITORING MYOCARDIAL ELECTRICAL STABILITY BY DETECTING PVC INDUCED T-WAVE ALTERNANS REVERSALS

FIELD OF THE INVENTION

The present invention generally relates to implantable systems, and methods for use therewith, for monitoring myocardial electrical stability by detecting PVC induced T-wave alternans reversals.

BACKGROUND

Electrical alternans relate to the differences in electrical potential at corresponding points between alternate heartbeats. T-wave alternans or alternation is a regular or beat-to-beat variation of the ST-segment or T-wave of an electrocardiogram (ECG) which repeats itself every beat group (e.g., two beats, three beats or four beats) and has been linked to underlying cardiac electrical instability. Typically, by enumerating all consecutive heart beats of a patient, beats with an odd number are referred to as "odd beats" and beats with an even number are referred to as "even beats." A patient's odd and even heartbeats may exhibit different electrical properties of diagnostic significance which can be detected from an ECG.

T-wave alternans may be caused by changes in ion exchange during repolarization. If there is an abrupt change in the repolarization period of one beat, the heart attempts to readjust on the following beat. This is manifested as an alternating change in the action potential duration. In the surface ECG this is seen primarily as a change in T-wave. For an implanted medical device such as a cardiac pacemaker, the electrogram (EGM) also shows a change in T-wave. Thus, the term T-wave as used herein may refer to a portion of the ventricular QRS-T-wave complex that includes the T-wave and the QRS-T segment. The alternating feature of T-wave alternans can be detected by examination, for example, of the QT interval, T-wave width, T-wave amplitude and morphology, etc.

T-wave alternans has been demonstrated in many studies as a strong predictor of mortality, independent of left ventricular ejection fraction (LVEF). More specifically, it has become well known that T-wave alternans have predictive value for arrhythmic events such as tachyarrhythmias. Additionally, T-wave alternans has been determined to be an indicator of various forms of disordered ventricular repolarization, including disorders found in patients with cardiomyopathy, mild to moderate heart failure, and congestive heart failure.

A recent publication by Narayan et al., entitled "T-wave alternans phase following ventricular extrasystoles predicts arrhythmia-free survival" (Heart Rhythm 2005, Vol 2, No 3: 234-41), which is incorporated herein by reference, concluded that phase reversal in T-wave alternans following single ventricular extrasystoles predicts spontaneous ventricular arrhythmias and all-cause mortality in patients with moderate ischemic left ventricular (LV) dysfunction and was a better predictor than positive T-wave alternans or programmed ventricular stimulation. However, the Narayan publication did not explain how its findings could be used outside of a clinical setting.

BRIEF SUMMARY OF THE INVENTION

Embodiments of the present invention relate to implantable systems, and methods for use therewith, for assessing a patients' myocardial electrical stability. Implanted electrodes of the implanted system are used to obtain an electrogram (EGM) signal, which is used to identify periods when the patient experiences T-wave alternans. Additionally, the EGM signal is used to determine whether premature ventricular contractions (PVCs) cause phase reversals of the T-wave alternans. The periods of T-wave alternans can be intrinsic, or they can be induced. The PVCs can be intrinsic, induced, or simulated.

The patient's myocardial electrical stability is assessed based on whether, and in a specific embodiment the extent to which, PVCs cause phase reversals of the T-wave alternans. In a specific embodiment, there is a determination of the percentage of the PVCs that cause phase reversals of the T-wave alternans, and the patient's myocardial electrical stability is assessed based on the determined percentage. In accordance with certain embodiments, the above described steps are repeated over time, in order to track changes in the patient's myocardial electrical stability.

A response can be triggered based on the assessment of the patient's myocardial electrical stability. For example, a first type of response can be triggered when the patient experiences T-wave alternans, but a PVC does not cause a phase reversal of the T-wave alternans; and a second (e.g., more aggressive) type of response can be triggered when the patient experiences T-wave alternans and a PVC causes a phase reversal of the T-wave alternans. Such responses may involve delivering anti-arrhythmia therapy. Alternatively, or additionally, responses can involve notifying a caregiver (e.g., physician, cardiac specialists, nurse, etc.). In a specific embodiment, if a PVC causes a phase reversal of the T-wave alternans, the response can be to charge a capacitor, in case the patient goes into ventricular fibrillation and needs shock therapy.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Figure 1:
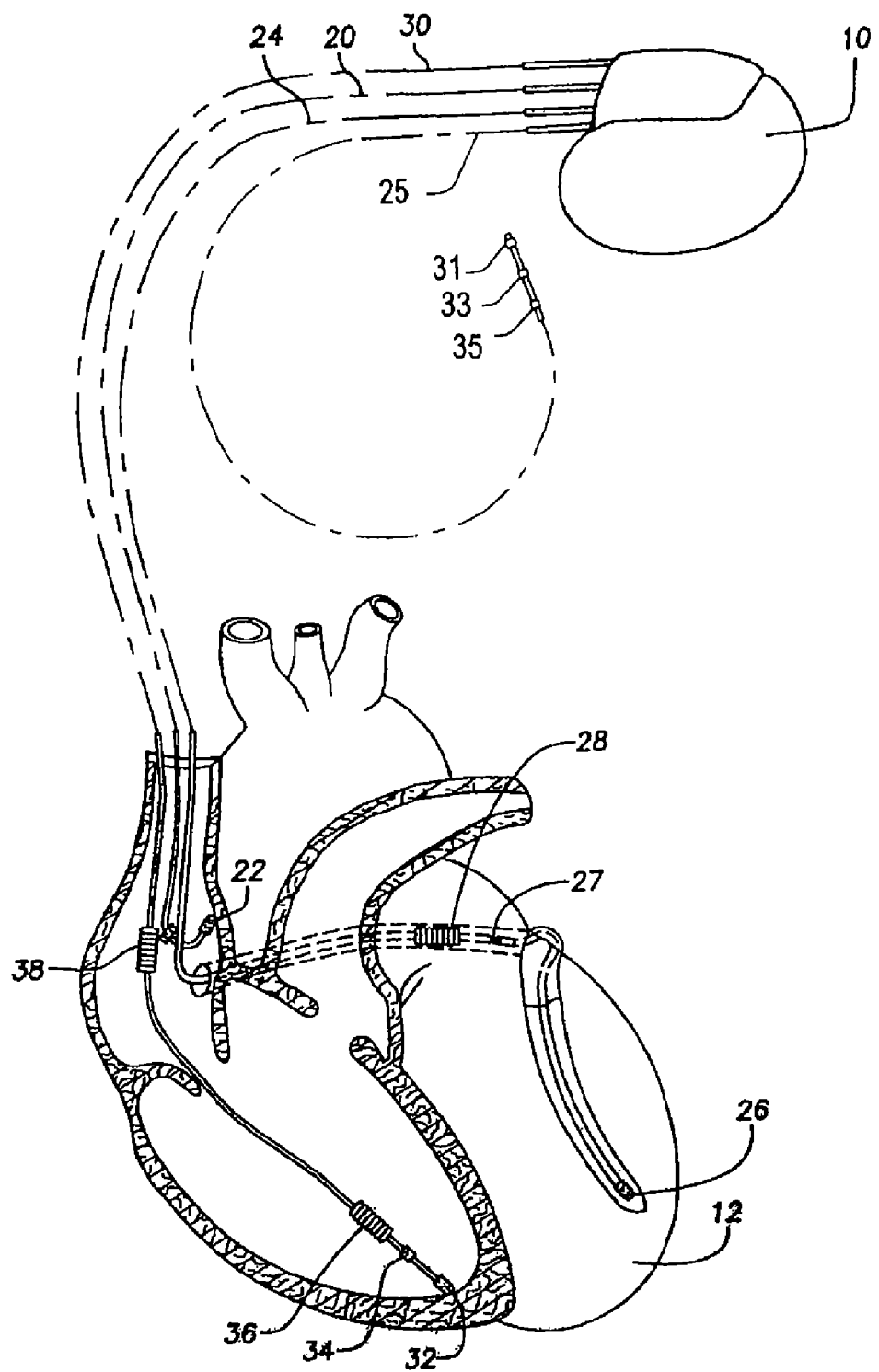
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
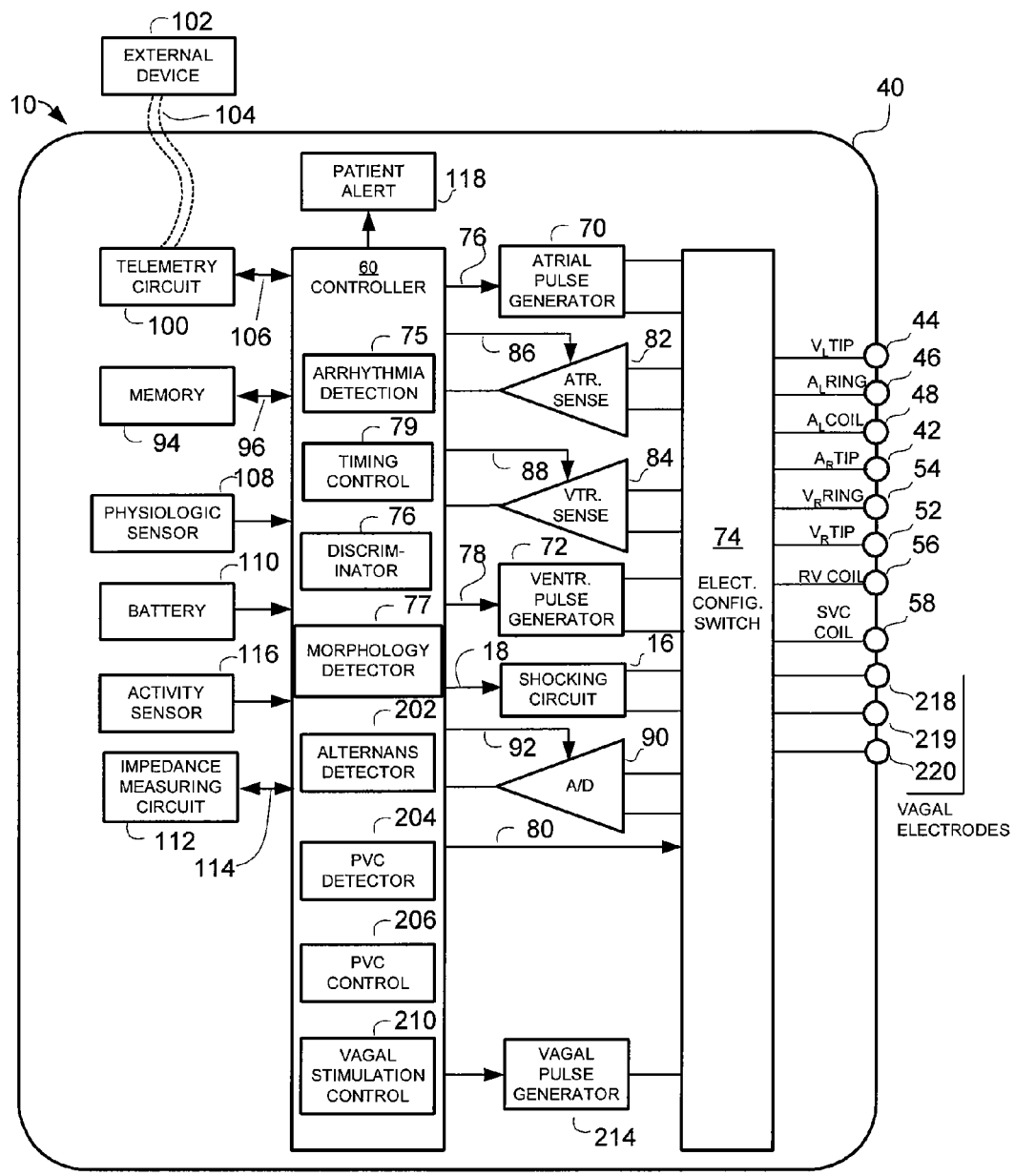
FIG. 2 is a functional block diagram of an exemplary ICD that can provide cardioversion, defibrillation, and pacing stimulation in four chambers of a heart, and detect the presence of electrical alternans, in accordance with an embodiment of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting T-wave alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

Still referring to FIG. 2, in accordance with embodiments of the present invention, the microcontroller 60 includes an alternans detector 202, which as described in more detail below, can detect the presence of T-wave alternans, as well as phase reversals of T-wave alternans. The alternans detector 202 can be implemented within the microcontroller 60, as shown in FIG. 2. Thus, alternans detector 202 can be implemented by software, firmware, or combinations thereof. It is also possible that all, or portions, of the alternans detector 202 can be implemented using hardware. Further, it is possible that all, or portions, of the alternans detector 202 be implemented external to the microcontroller 60.

In an embodiment, the alternans detector 202 triggers data acquisition circuit 90 and timing control circuit 79 to record an electrogram (EGM) signal. Using the EGM signal, alternans detector 202 can measure metrics of the signal (e.g., T-wave metrics), such as T-wave amplitude, T-wave width, T-wave slope, T-wave area, T-wave morphology, QT interval, evoked QT interval, etc. in the EGM signal generated by the sensing circuits of the data acquisition system 90. Metrics of other portions of the EGM signal, other than the T-wave, can alternatively or additionally be measured. The alternans detector 202 can also trigger the implantable device 10 to respond appropriately when T-wave alternans are detected, as will be explained in more detail below. Additionally, in conjunction with the telemetry circuit 100, the alternans detector 202 can be configured to deliver status information, relating to the patient's T-wave alternans, to the external device 102 through an established communication link 104. The alternans detector 202 may also trigger a patient or physician alert in response to detecting T-wave alternans. For example, a patient alert 118, which produces a vibratory or auditory alert, may be triggered by the alternans detector 202.

Still referring to FIG. 2, in accordance with embodiments of the present invention, the microcontroller 60 includes a premature ventricular contraction (PVC) detector 204, that can detect premature ventricular contractions (PVCs). An intrinsic (i.e., naturally occurring) PVC can be caused by a ventricular premature beat (VPB). An intrinsic PVC may also be caused by a naturally occurring intrinsic premature atrial contraction (PAC), which conducts through the AV node and into the ventricles, thereby causing the ventricles to prematurely contract. The PVC detector 204 can detect an intrinsic PVC, e.g., by monitoring cardiac intervals (e.g., RR intervals), and detecting when the length of a cardiac interval is shortened beyond a threshold, as compared to the previous (or an average of a plurality of previous cardiac intervals). This is just one example. Other techniques for detecting intrinsic PVCs are also within the scope of the present invention. A disadvantage of relying on intrinsic PVCs, however, is that they cannot be executed on-demand or at regular intervals.

The microcontroller 60 also includes a PVC controller 206 that can be used to induce PVCs. An induced PVC is also known as a premature ventricular stimulation (PVS). Referring to FIG. 2, a PVC can be induced, e.g., by applying a single premature stimulus to the one of the ventricles using the ventricular pulse generator 72. A disadvantage of this technique, however, is that artificially inducing PVCs may cause an arrhythmia. It is also possible that PVCs can be induced, on demand, by inducing premature atrial contractions (PACs). In such an approach, the patient's right or left atrium is stimulated prematurely to artificially induce a PAC. Referring back to FIG. 2, this can be accomplished by applying a single premature stimulus to the atrium using the pulse generator 70. The induced PAC conducts through the AV node and into the ventricles, thereby causing the ventricles to prematurely contract, which results in a corresponding drop in blood pressure. An advantage of this technique is that it can be executed on-demand and at regular intervals, and is not likely to cause an arrhythmia.

The PVC controller 206 can also simulate PVCs, as explained below. An arterial blood pressure disturbance can be triggered by stimulating a patient's vagus nerve, as was disclosed in commonly invented and assigned U.S. patent application Ser. No. 10/861,747, entitled "System and Method for Using Vagal Stimulation to Assess Autonomic Tone and Risk of Sudden Cardiac Death in an Implantable Cardiac Device," filed Jun. 4, 2004, which is incorporated herein by reference. As explained in the '747 application, a short burst of stimulation to the vagus nerve induces a drop in atrial pressure, which simulates a patient's cardiovascular response to a premature contraction of the ventricles. Accordingly, such stimulation of the vagus nerve will be referred to hereafter as "simulating" a PVC. This is accomplished by delivering, on demand, a short burst of stimulation to the vagus nerve to thereby induces a drop in atrial pressure, which simulates a patient's cardiovascular response to a premature contraction of the ventricles. More specifically, the patient's vagus nerve is stimulated for a duration that simulates a compensatory pause, in order to trigger an intrinsic baroreflex response to a drop in blood pressure. Referring back to FIG. 1, the vagal stimulation lead 25 can be used to deliver such stimulation. Referring to FIG. 2, the vagal pulse generator 214 can produce the stimulation pulses delivered by the lead 25.

In accordance with an embodiment of the present invention, information related to PVCs can be stored. This can include, for example, storing timing and location information relative to the T-wave alternans. Such information can be continually, or from time to time, automatically uploaded to an external device (e.g., 102) located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

Figure 3:
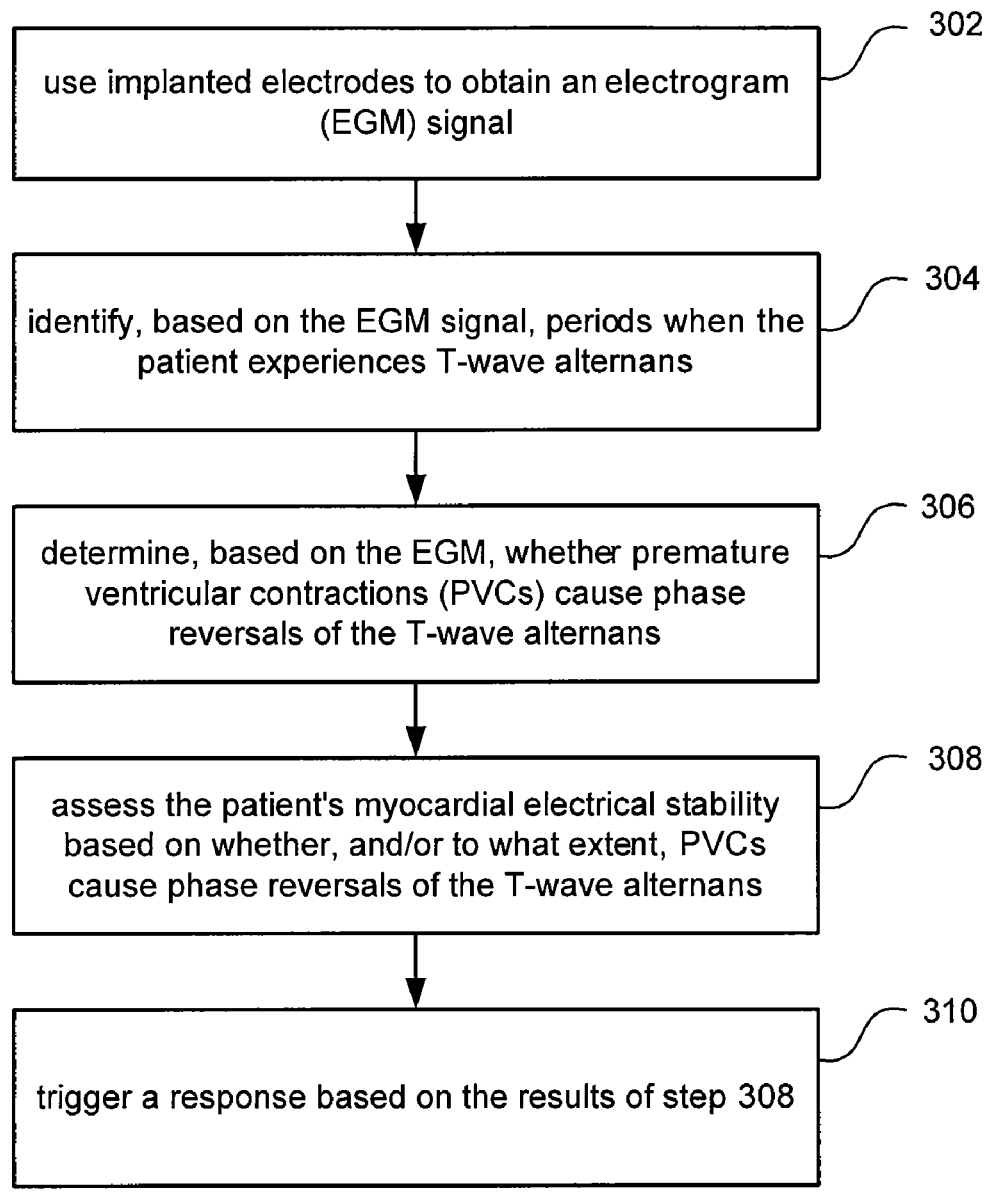
FIG. 3 is a high-level flow diagram that is useful for describing embodiments of the present invention that are used to monitor myocardial electrical stability.

Specific embodiments of the present invention will now be summarized with reference to the high level flow diagram of FIG. 3, where the various algorithmic steps are summarized in individual "blocks". Such blocks describe specific actions or decisions that are made or carried out as the algorithm proceeds. Where a microcontroller (or equivalent) is employed, the flow diagram presented herein provide the basis for a "control program" that may be used by such a microcontroller (or equivalent) to effectuate the desired control of the cardiac device. Those skilled in the art may readily write such a control program based on the flow diagram and other descriptions presented herein. The steps of the flow diagram can be implemented by an implantable cardiac device, such as but not limited to ICD 10.

At a step 302, an electrogram (EGM) signal is obtained using implanted electrodes of an implanted system, such as those discussed above with regards to FIGS. 1 and 2. The obtained EGM signal can be cleaned up, e.g., by filtering the signal and/or removing segments of noisy beats. Filtering the signal could include, e.g., the use of a low-pass filter with a cutoff frequency of about 250 Hz. Additionally, a high-pass filter can be used to reduce the contribution of DC-offsets and respiration drift to the signal. Removal of noisy beats can be accomplished, e.g., by removing any number of RR intervals of beats that are exposed to severe noise, e.g., from myopotentials or electromagnetic interference.

At a step 304, periods when the patient experiences T-wave alternans are identified based on the EGM. T-wave alternans or alternation, as referred to hereafter, is a regular or beat-to-beat variation of the ST-segment or T-wave of an EGM which repeats itself every beat group (e.g., two beats, three beats or four beats). There are numerous techniques for detecting T-wave alternans, either in the time domain or the frequency domain, many of which can be used for step 304. Some exemplary techniques, which are not meant to be limiting, are discussed below with reference to FIGS. 4A, 4B, 5A and 5B. However, the use of alternative techniques are also within the scope of the present invention.

The T-wave alternans can be intrinsic, or they can be induced. As explained above, alternans detector 202 can be used to detect intrinsic PVCs. Alternatively, or additionally, T-wave alternans can be induced by pacing the patient at an elevated constant heart rate that should reveal the presence of T-wave alternans. In other embodiments, T-wave alternans are induced by pacing the patient using a patterned pacing sequence, which are believed to produce T-wave alternans with higher amplitudes. The alternans detector 202 can be used to confirm whether and when T-wave alternans have been induced.

An example of a patterned pacing sequence, used to induce T-wave alternans, is one in which a relatively shorter interval occurs periodically once every fourth cycle during a moderately fast and constant pacing routine. This is an example of a patterned pacing sequence that repeats every 4 beats. Other examples of patterned pacing sequences are disclosed in U.S. patent application Ser. No. 10/884,276 (Bullinga), filed Jan. 6, 2005, (Publication No. US 2005/0004608), entitled "System and Method for Assessment of Cardiac Electrophysiologic Stability and Modulation of Cardiac Oscillations," which is incorporated herein by reference. Further examples of patterned pacing sequences are disclosed in U.S. patent application Ser. No. 11/341,086 (Farazi), filed Jan. 26, 2006, entitled "Pacing Schemes For Revealing T-wave Alternans (TWA) at Low to Moderate Heart Rates," which is also incorporated herein by reference.

By pacing a patient's heart with a patterned pacing sequence, the expected alternans pattern is known. For example, if the patterned pacing sequence repeats every 3 beats, then it is expected that there will be an ABCABCABC . . . alternans pattern; if the patterned pacing sequence repeats every 4 beats, then it is expected that there will be an ABCD-ABCDABCD . . . alternans pattern; and so on. In accordance with specific embodiments of the present invention, because patterned pacing sequences are being used to induce specific expected alternans patterns, analysis of the alternans can be optimized to match the pattern being induced.

In accordance with an embodiment of the present invention, information related to the T-wave alternans can be stored. This can include, for example, storing amplitude, slope, timing, and/or duration information relating to the alternans. Such information can be continually, or from time to time, automatically uploaded to an external device (e.g., 102). Such an external device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

At a step 306, there is a determination, based on the EGM, of whether premature ventricular contractions (PVCs) cause phase reversals of the T-wave alternans. A phase reversal (also known as a phase inversion) occurs when there is a change in the phase of a T-wave alternans pattern, e.g., from ABAB . . . type pattern to a BABA . . . type pattern, where A and B represent higher and lower metrics of connective values of ST-segments or T-waves. There are numerous techniques for detecting such phase reversals, many of which can be used at step 306. An exemplary technique for detecting phase reversals is discussed below with reference to FIGS. 6A and 6B. However, use of other alternative techniques are also within the scope of the present invention.

At a step 308, there is an assessment of the patient's myocardial electrical stability, based on whether, and in specific embodiments the extent to which, PVCs cause phase reversals of the T-wave alternans. This can include, for example, determining what percentage of the PVCs cause phase reversals of the T-wave alternans, and assessing the myocardial electrical stability based on the determined percentage. In such embodiments, the greater the extent to which PVCs cause phase reversals, the worse the patient's myocardial electrical stability, which is indicative of a the patients risk of an arrhythmia, and risk sudden cardiac death (SCD).

At a step 310, a response of the implantable system is triggered, based on the results of step 308. T-wave alternans, themselves, are indicative of myocardial electrical instability. However, phase reversals of T-wave alternans following PVCs are believed to be indicative of an even greater myocardial electrical instability, and thus a heightened risk of a ventricular arrhythmia, such as a tachyarrhythmia. Accordingly, in an embodiment, a patient is alerted (e.g., using alert 118) when the implantable system assesses that the patient's myocardial electrical stability drops below a threshold (or, stated another way, that the patient's myocardial instability exceeds a threshold). Such an alert could be a vibratory or auditory alert that originates from within the implantable device 10. Alternatively, the implantable device 10 may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible the a tachyarrhythmias may be avoided, or if it does occur, the patient will be less dangerous to themselves and others if the patient is resting when the tachyarrhythmias occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever the presence of electrical alternans is detected.

In further embodiments, therapy can be triggered in response to detecting the presence of T-wave alternans, or a phase reversal of T-wave alternans induced by a PVC. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate drug therapy. In still another embodiment, the implanted device, if appropriately equipped, can deliver appropriate pacing therapy, including but not limited to anti-tachycardia pacing. In still another embodiment, the implantable device, if cable of delivering shock therapy, can begin to charge its capacitors in case the patient goes into ventricular fibrillation and needs shock therapy. These are just a few examples of the types of responses that can be performed. One of ordinary skill in the art would understand from the above description that other responses are also possible, while still being within the spirit and scope of the present invention.

At step 310 one of a plurality of different responses can be selected by the implanted device (e.g., 10), based on the results of step 308. For example, it may be that a first type of response is triggered if the patient is experiencing T-wave alternans, but one or more PVC did not cause phase reversal(s) of the T-wave alternans; and that a more aggressive second type of response is triggered if one or more PVC caused phase reversal(s) of the T-wave alternans. For a more specific example, the first type of response can be an alert and/or delivery of anti-tachycardia pacing therapy, and the more aggressive second type of response could be to begin to charge a capacitor in case the patient goes into ventricular fibrillation and needs shock therapy. The triggering of the second type of response can be in place of the first type of response, or in addition to the first type of response. Use of other types of different responses, are also within the scope of the present invention.

In further embodiments, changes in the patient's myocardial electrical stability are tracked, by using the embodiments described above, and one or more of the above described responses can be triggered if a change in the patient's myocardial electrical stability exceeds a corresponding threshold, or if the patient's myocardial electrical stability falls below a threshold. For example, if the percentage of PVCs that cause phase reversals of T-wave alternans increases over time, then it can be determined that the patient's myocardial electrical stability is worsening (and that the risk of an arrhythmia or SCD is increasing). If the percentage of PVCs that cause phase reversals of T-wave alternans decreases over time, then it can be determined that the patient's myocardial electrical stability is improving (and that the patient's risk of an arrhythmia or SCD is decreasing).

Steps 302-308 can be continually repeated, performed from time to time (e.g., periodically), or they can occur in response to a triggering event. It is likely that step 302 occurs substantially continually, since an obtained EGM is used in various algorithms. However, it may be that steps 304-308 only occur when there is an increase probability that the patient will experience T-wave alternans, such as when the patient's heart rate (e.g., as detected from an EGM) exceeds a threshold (e.g., 150 bpm), when a patient's activity level (e.g., as detected using an activity sensor 116) exceeds a threshold, or when the patient is paced in a manner that may reveal T-wave alternans. By performing steps 304-308 less often, resources, such as processing resources and battery power, can be conserved.

As mentioned above, there are numerous ways in which T-wave alternans can be detected, many of which can be used with embodiments of the present invention. For example, one way to detect an ABAB . . . alternans pattern (i.e., a two beat alternans pattern) at step 304, is to divide a plurality of consecutive beats into a plurality of sets (pairs, in this instance) of consecutive beats. For example, assume that the desire is to determine whether T-wave alternans are present based on 250 sets of 2 consecutive beats (i.e., each set includes a beat pattern AB). Also assume that the metric being measured for each beat is T-wave amplitude. The T-wave amplitudes of the 250 "A" beats can be averaged, the T-wave amplitudes of the 250 "B" beats can be average. A difference between the average "A" T-wave amplitude and the average "B" T-wave amplitude can then be determined, and a determination of whether T-wave alternans are present can then be based on whether such difference exceeds a corresponding threshold. A potential problem with performing the averaging suggested above is that such averaging may mask or bury important information included within the sets (e.g., pairs) of consecutive beats. For example, if there is a phase reversal within one of the sets, the averaging as suggested above may mask such information.

Accordingly, it is preferred that one or more pairwise combination of consecutive pairs of beats are determined for each of the plurality of sets (e.g., pairs, in this example) of consecutive beats. For example, each pairwise combination can be a pairwise difference. In other words, the pairwise combination for beat pair AB (referred to as $S_{AB}$) is equal to a metric of beat A minus a corresponding metric of beat B (i.e., $S_{AB}$=metric A−metric B). In accordance with specific embodiments, the metric of a beat is a T-wave metric, such as, but not limited to T-wave amplitude, T-wave width, T-wave slope, T-wave area, T-wave morphology, QT interval, and evoked QT interval. For simplicity, it will be assumed that the metric being used is T-wave amplitude. Thus, an exemplary pairwise combination for beat pair AB is equal to the T-wave amplitude of beat A minus the T-wave amplitude of beat B (i.e., $S_{AB}$=T-wave amplitude (A)−T-wave amplitude (B)). Continuing with the example that 500 beats are separated into 250 pairs of consecutive beats, this will result in 250 $S_{AB}$ values (e.g., $S_{AB1}$=T-wave amplitude ($A_1$)−T-wave amplitude ($B_1$); $S_{AB2}$=T-wave amplitude ($A_2$)−T-wave amplitude ($B_2$); $S_{AB3}$=T-wave amplitude ($A_3$)−T-wave amplitude ($B_3$), etc.). T-wave alternans can then be detected by comparing the pairwise differences to a corresponding threshold, and detecting T-wave alternans when pairwise differences exceed the threshold.

Alternatively, each pairwise combination can be a pairwise summation. In other words, the pairwise combination for beat pair AB (referred to as $S_{AB}$) can be equal to a metric of beat A plus a corresponding metric of beat B (i.e., $S_{AB}$=metric A+metric B). In still another embodiment of the present invention, each pairwise combination determined at step 402 can be a pairwise average. In other words, the pairwise combination for beat pair AB (referred to as $S_{AB}$) can be equal to an average of a metric of beat A and a metric of beat B (i.e., $S_{AB}$=avg (metric A+metric B)). These are just a few examples of pairwise combinations. Other types of pairwise combinations are also within the scope of the present invention. Corresponding pairwise combinations can then be cumulative averaged or cumulative summed to thereby produce a plurality of cumulative values (G). For example, where the pairwise combinations are cumulative averaged, then $G_n$=avg ($S_1+S_2 \ldots +S_n$), e.g., $G_{AB1}$=$S_{AB1}$; $G_{AB2}$=avg ($S_{AB1}+S_{AB2}$); $G_{AB3}$=avg ($S_{AB1}+S_{AB2}+S_{AB3}$); . . . and $G_{ABn}$=avg ($S_{AB1}+S_{AB2}+S_{AB3} \ldots +S_{ABn}$). Where the pairwise combinations are cumulative sums, then the cumulative values $G_n$=sum ($S_1+S_2 \ldots +S_n$), e.g., $G_{AB1}$=$S_{AB1}$; $G_{AB2}$=sum ($S_{AB1}+S_{AB2}$); $G_{AB3}$=sum ($S_{AB1}+S_{AB2}+S_{AB3}$); . . . and $G_{ABn}$=sum ($S_{AB1}+S_{AB2}+S_{AB3} \ldots +S_{ABn}$).

Figure 4A:
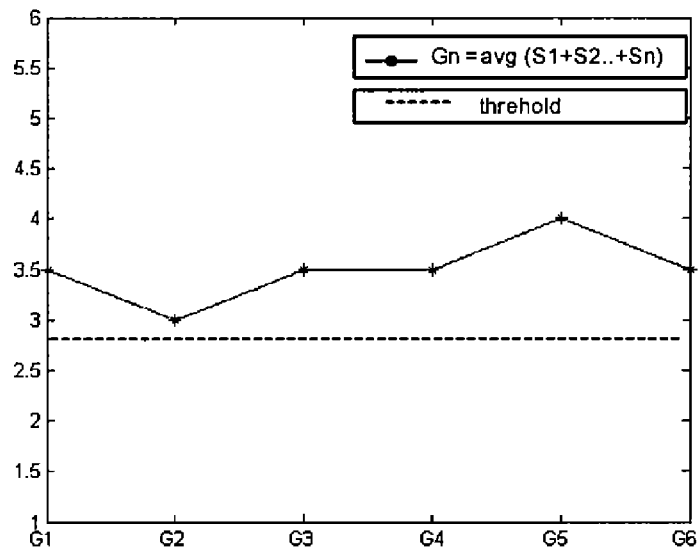
FIGS. 4A and 4B are graphs that are useful for describing how cumulative average values can be used to detect the presence of electrical alternans.
Figure 4B:
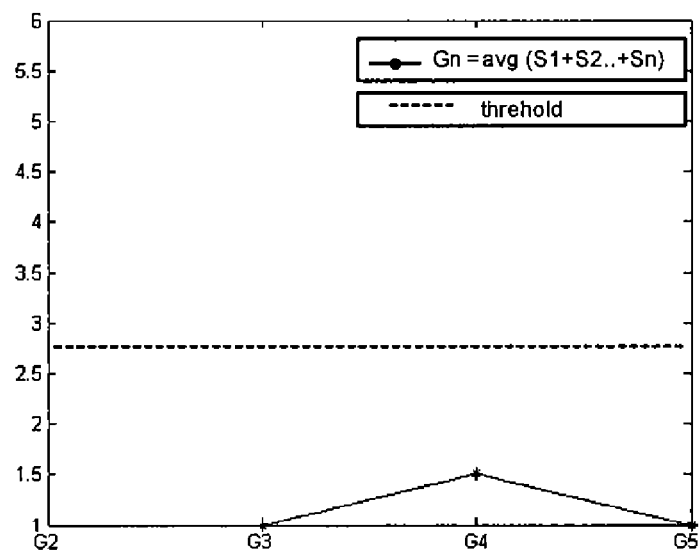

FIG. 4A is a graph of cumulative average values when T-wave alternans are present, and FIG. 4B is a graph of cumulative average values when T-wave alternans are not present. As can be appreciated from FIGS. 4A and 4B, when T-wave alternans are present the cumulative average values remain above a threshold (represented by a dashed line), and when T-wave alternans are not present the cumulative average values remain below the threshold. Accordingly, in embodiments where cumulative values (G) are cumulative average values, the presence of T-wave alternans can be determined by comparing cumulative average values to a threshold. Such a threshold can be determined, e.g., through experimentation. The threshold can be specific to a patient, or specific to a population.

Figure 5A:
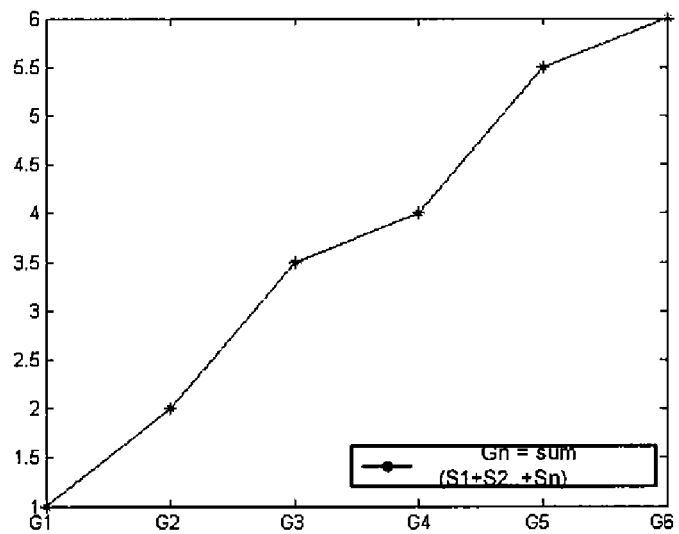
FIGS. 5A and 5B are graphs that are useful for describing how cumulative sum values can be used to detect the presence of electrical alternans.
Figure 5B:
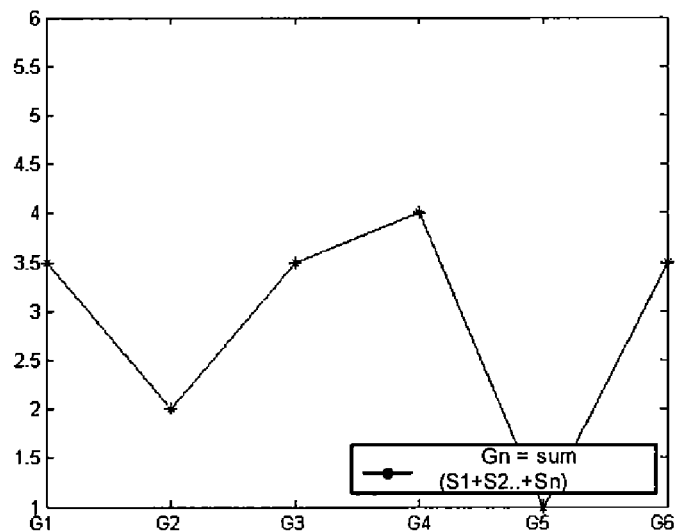

FIG. 5A is a graph of cumulative sum values when T-wave alternans are present, and FIG. 5B is a graph of cumulative sum values when T-wave alternans are not present. As can be appreciated from FIGS. 5A and 5B, where T-wave alternans are present the cumulative sum values continually increase, and where T-wave alternans are not present the cumulative sum values do not continually increase (but rather, go up and down in a generally random manner). Accordingly, in embodiments where cumulative values (G) are cumulative sum values, the presence of T-wave alternans can be determined, e.g., by comparing a slope of the cumulative sum values to a slope threshold. Alternatively, it can be determined that T-wave alternans are present when at least a specific number of consecutive cumulative sum values increase in value.

Figure 6A:
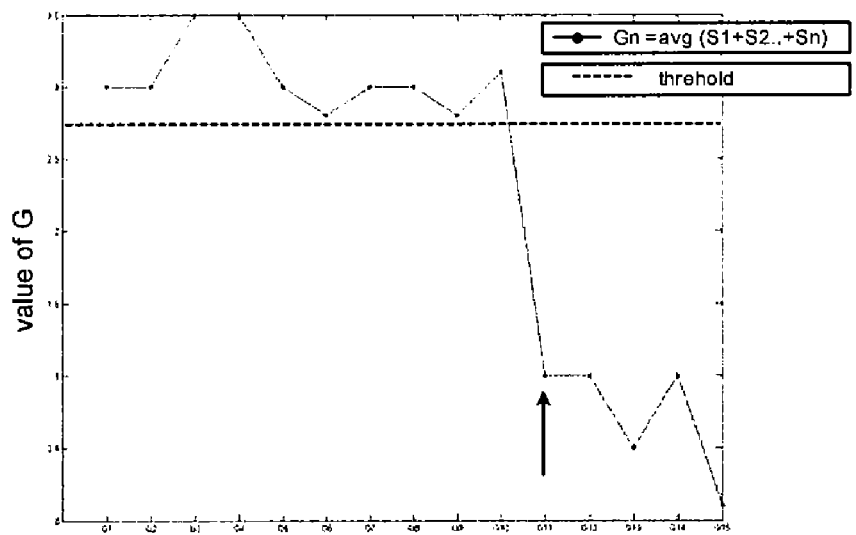
FIG. 6A is a graph that is useful for describing how cumulative average values can be used to detect phase reversals of T-wave alternans.

FIG. 6A is a graph of cumulative average values when T-wave alternans are present and a phase reversal occurs. In this example, the phase reversal can be detected when the cumulative average values stay consistently within one range of values and then suddenly shift into another (e.g., lower) range of values, e.g., within a few beats or specified short amount of time. For example, if at least X consecutive cumulative average values are within a predefined range, followed by at least X further consecutive cumulative average values within a different predefined range, then it can be determined that a phase reversal occurred. The arrow in FIG. 6A shows that a phase reversal occurs in $11^{th}$ pair of beats which was used to determine pairwise combination $S_{11}$.

Figure 6B:
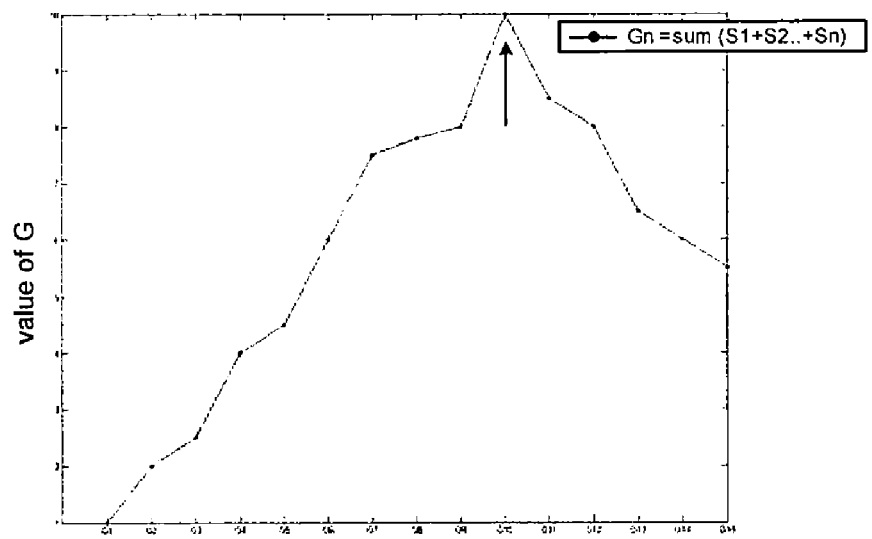
FIG. 6B is a graph that is useful for describing how cumulative sum values can be used to detect phase reversals of T-wave alternans.

FIG. 6B is a graph of cumulative sum values when T-wave alternans are present and a phase reversal occurs. In this example, the phase reversal can be detected when the cumulative sum values consistently increase for a predetermined number of beats or amount of time, and then suddenly consistently decrease for a predetermined number of beats or amount of time. For example, if there are at least X consecutive cumulative sum values that increase in value, followed by at least X further consecutive cumulative sum values that decrease in value, then it can be determined that a phase reversal caused the sudden change in cumulative average values. For another example, if the cumulative values have a consistently positive slope followed by a consistently negative slope, then it can be determined that a phase reversal caused the sudden change in slope of cumulative values. The arrow in FIG. 6B shows that the phase reversal occurs in $11^{th}$ pair of beats which was used to determine pairwise combination $S_{11}$.

A determination of whether such a phase reversal was caused by a PVC can be performed in various manners. For example, if there was a PVC that immediately proceeded the phase reversal, it can be assumed that the phase reversal was due to the PVC. In specific embodiments, it can be assumed that the PVC caused the phase reversal if the PVC occurred within a specified time and/or number of beats prior to the phase reversal. Other variations are also possible, and within the scope of the present invention.

These are just a few ways in which phase reversals of T-wave alternans can be detected, which are not meant to be limiting. Other techniques for detecting phase reversals of T-wave alternans are also within the scope of the present invention. Further, other time domain techniques, as well as frequency domain techniques, for detecting T-wave alternans in the first place are also within the scope of the present invention. For example, the Bullinga and Farazi applications, which were incorporated by reference above, discuss other time domain and frequency domain techniques for detecting T-wave alternans. Additionally, the Bullinga application discusses additional ways in which phase reversals (referred to a phase inversions in the Bullinga application) can be detected.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable system, a method for assessing a patient's myocardial electrical stability, comprising:
   (a) obtaining an electrogram (EGM) signal using implanted electrodes;
   (b) identifying, based on the EGM, periods when the patient experiences T-wave alternans;
   (c) determining, based on the EGM, whether premature ventricular contractions (PVCs) cause phase reversals of the T-wave alternans;
   (d) determining what percentage of the PVCs cause phase reversals of the T-wave alternans;
   (e) assessing the patient's myocardial electrical stability based on the determined percentage; and
   (f) triggering a response based on the results of step (e), wherein step (f) includes:
      triggering a first type of response when the patient experiences T-wave alternans, but a PVC does not cause a phase reversal of the T-wave alternans; and
      triggering a second type of response when the patient experiences T-wave alternans and a PVC causes a phase reversal of the T-wave alternans, wherein the second type of response is different from the first type of response and wherein the second type of response includes charging a capacitor.

2. The method of claim 1, wherein step (c) includes at least one of, while the patient is experiencing T-wave alternans:
   detecting an intrinsic PVC;
   inducing a PVC; and
   simulating a PVC.

3. The method of claim 1, further comprising tracking changes in the patient's myocardial electrical stability as steps (a), (b), (c), (d), and (e) are repeated over time.

4. The method of claim 1, wherein steps (b) and (c) are preformed in response to the patient's heart rate exceeding a corresponding threshold, or in response to the patient's activity level exceeding a corresponding threshold.

5. The method of claim 1, wherein step (b) includes:
   dividing a plurality of consecutive beats into a plurality of sets of consecutive beats;
   determining for the plurality of sets a pairwise combination.

6. A non-transitory computer readable medium having instructions that when executed on a processor of an implantable medical device having cardiac pacing capabilities cause the IMD to:

obtain an electrogram (EGM) signal using implanted electrodes;
identify, based on the EGM, periods when the patient experiences T-wave alternans;
determine, based on the EGM, whether premature ventricular contractions (PVCs) cause phase reversals of the T-wave alternans;
determine what percentage of the PVCs cause phase reversals of the T-wave alternans;
assess the patient's myocardial electrical stability based on the determined percentage;
correlate a phase reversal of the T-wave alternans following a PVC with myocardial electrical instability, wherein the greater the extent to which PVCs cause phase reversals, the worse the patient's myocardial instability;
trigger a first type of response when the patient experiences T-wave alternans, but a PVC does not cause a phase reversal of the T-wave alternans, wherein the first type of response is an alert and/or a therapeutic response; and
trigger a second type of response when the patient experiences T-wave alternans and a PVC causes a phase reversal of the T-wave alternans, wherein the second type of response is a therapeutic response and is therapeutically more aggressive than the first type of response.

7. The computer readable medium of claim 6, wherein the instructions further cause the IMD to at least one of, while the patient is experiencing T-wave alternans:
detect an intrinsic PVC;
induce a PVC; and
simulate a PVC.

8. The computer readable medium of claim 6, wherein the instructions further cause the IMD to track changes in the patient's myocardial electrical stability over time by determining whether the percentage of PVCs that cause phase reversals of T-wave alternans changes over time.

9. In an implantable system, a method for assessing a patient's myocardial electrical stability, comprising:
  (a) obtaining an electrogram (EGM) signal using implanted electrodes;
  (b) identifying, based on the EGM, periods when the patient experiences T-wave alternans, wherein step (b) includes dividing a plurality of consecutive beats into a plurality of sets of consecutive beats and determining for the plurality of sets a pairwise combination, wherein the pairwise combination is a pairwise difference, wherein the pairwise difference is equal to a metric of the first beat in the pairwise combination minus a metric of the second beat in the pairwise combination;
  (c) determining, based on the EGM, whether premature ventricular contractions (PVCs) cause phase reversals of the T-wave alternans;
  (d) determining what percentage of the PVCs cause phase reversals of the T-wave alternans; and
  (e) assessing the patient's myocardial electrical stability based on the determined percentage.

10. In an implantable system, a method for assessing a patient's myocardial electrical stability, comprising:
  (a) obtaining an electrogram (EGM) signal using implanted electrodes;
  (b) identifying, based on the EGM, periods when the patient experiences T-wave alternans, wherein step (b) includes dividing a plurality of consecutive beats into a plurality of sets of consecutive beats and determining for the plurality of sets a pairwise combination, wherein the pairwise combination is a pairwise summation, wherein the pairwise summation is equal to a metric of the first beat in the pairwise combination plus a metric of the second beat in the pairwise combination;
  (c) determining, based on the EGM, whether premature ventricular contractions (PVCs) cause phase reversals of the T-wave alternans;
  (d) determining what percentage of the PVCs cause phase reversals of the T-wave alternans; and
  (e) assessing the patient's myocardial electrical stability based on the determined percentage.

11. In an implantable system, a method for assessing a patient's myocardial electrical stability, comprising:
  (a) obtaining an electrogram (EGM) signal using implanted electrodes;
  (b) identifying, based on the EGM, periods when the patient experiences T-wave alternans, wherein step (b) includes dividing a plurality of consecutive beats into a plurality of sets of consecutive beats and determining for the plurality of sets a pairwise combination, wherein the pairwise combination is a pairwise average, wherein the pairwise average is equal to an average of a metric of the first beat in pairwise combination and a metric of the second beat in the pairwise combination;
  (c) determining, based on the EGM, whether premature ventricular contractions (PVCs) cause phase reversals of the T-wave alternans;
  (d) determining what percentage of the PVCs cause phase reversals of the T-wave alternans; and
  (e) assessing the patient's myocardial electrical stability based on the determined percentage.

12. In an implantable system, a method for assessing a patient's myocardial electrical stability, comprising:
  (a) obtaining an electrogram (EGM) signal using implanted electrodes;
  (b) identifying, based on the EGM, periods when the patient experiences T-wave alternans, wherein step (b) includes dividing a plurality of consecutive beats into a plurality of sets of consecutive beats and determining for the plurality of sets a pairwise combination, wherein step (b) further includes cumulative averaging corresponding pairwise combinations to produce a plurality of cumulative average values;
  (c) determining, based on the EGM, whether premature ventricular contractions (PVCs) cause phase reversals of the T-wave alternans;
  (d) determining what percentage of the PVCs cause phase reversals of the T-wave alternans; and
  (e) assessing the patient's myocardial electrical stability based on the determined percentage.

13. The method of claim 12 wherein step (b) further includes identifying T-wave alternans to be present when the cumulative average values remain above a threshold and identifying T-wave alternans not to be present when the cumulative average values remain below a threshold.

14. The method of claim 12 wherein step (c) includes: detecting phase reversals of the T-wave alternans when the cumulative average values stay consistently within one range of values and then within a predetermined number of beats or amount of time shift into a different range of values.

15. In an implantable system, a method for assessing a patient's myocardial electrical stability, comprising:
  (a) obtaining an electrogram (EGM) signal using implanted electrodes;
  (b) identifying, based on the EGM, periods when the patient experiences T-wave alternans, wherein step (b) includes dividing a plurality of consecutive beats into a plurality of sets of consecutive beats and determining for the plurality of sets a pairwise combination, wherein step (b) further includes cumulative summing corresponding pairwise combinations to produce a plurality of cumulative sum values;

(c) determining; based on the EGM, whether premature ventricular contractions (PVCs) cause phase reversals of the T-wave alternans;

(d) determining what percentage of the PVCs cause phase reversals of the T-wave alternans; and (e) assessing the patient's myocardial electrical stability based on the determined percentage.

16. The method of claim 15 wherein step (b) further includes identifying T-wave alternans to be present when the cumulative sum values continually increase and identifying T-wave alternans not to be present when the cumulative sum values go up and down in a generally random manner.

17. The method of claim 15 wherein the presence of T-wave alternans is determined by comparing the slope of the cumulative sum values to a slope threshold.

18. The method of claim 15 wherein it is determined that T-wave alternans are present when at least a specific number of consecutive cumulative sum values increase in number.

19. The method of claim 15 wherein step (c) includes: detecting phase reversals of the T-wave alternans when the cumulative sum values consistently increase for a predetermined number of beats or amount of time, and then suddenly consistently decrease for a predetermined number of beats or amount of time.

20. The method of claim 15 wherein step (c) includes: detecting phase reversals of the T-wave alternans when the cumulative sum values have a consistently positive slope followed by a consistently negative slope.

* * * * *